United States Patent
Leichner et al.

(12) 
(10) Patent No.: US 6,696,024 B1
(45) Date of Patent: Feb. 24, 2004

(54) DEVICE FOR THE CAPILLARY TRANSPORT OF LIQUID

(75) Inventors: Wilhelm Leichner, Mannheim (DE); Wolfgang Schwobel, Mannheim (DE); Volker Zimmer, Dossenheim (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/554,815

(22) PCT Filed: Dec. 3, 1998

(86) PCT No.: PCT/EP98/07852

§ 371 (c)(1), (2), (4) Date: Sep. 21, 2000

(87) PCT Pub. No.: WO99/29497

PCT Pub. Date: Jun. 17, 1999

(30) Foreign Application Priority Data

Dec. 4, 1997 (DE) .......... 197 53 851

(51) Int. Cl.[7] .............. G01N 21/84
(52) U.S. Cl. .......... 422/100; 422/58; 436/180; 436/170
(58) Field of Search .............. 422/56, 61, 99–100, 422/102, 104; 436/164, 166, 169, 170, 180

(56) References Cited

U.S. PATENT DOCUMENTS

| | | | |
|---|---|---|---|
| 3,715,192 A | 2/1973 | Wenz et al. | 23/253 TP |
| 5,192,502 A | 3/1993 | Attridge et al. | 422/57 |
| 5,503,803 A | 4/1996 | Brown | 422/102 |
| 5,814,522 A * | 9/1998 | Zimmer et al. | 436/170 |
| 5,846,837 A * | 12/1998 | Thym et al. | 436/170 |
| 5,998,224 A * | 12/1999 | Rohr et al. | 436/526 |
| 6,207,000 B1 * | 3/2001 | Schwobel et al. | 156/248 |

FOREIGN PATENT DOCUMENTS

| | | |
|---|---|---|
| EP | 0 034 049 B1 | 8/1981 |
| EP | 0 287 883 A1 | 10/1988 |
| EP | 0 348 006 A2 | 12/1989 |
| EP | 0 487 068 A1 | 5/1992 |

* cited by examiner

*Primary Examiner*—Lyle A. Alexander
(74) *Attorney, Agent, or Firm*—Jill L. Woodburn

(57) ABSTRACT

The invention concerns a device for the capillary transport of a liquid between two opposite, essentially planar layers, in which the two layers are arranged parallel to one another at such a distance that there is a capillary-active gap between the two layers, wherein at least one of the two layers contains at least two discrete adjacent parts and capillary-active transport of the liquid is possible beyond the common boundary of the parts that lie in one layer.

24 Claims, 1 Drawing Sheet

DEVICE FOR THE CAPILLARY TRANSPORT OF LIQUID

The invention concerns a device for the capillary transport of a liquid between two opposite, essentially planar layers, in which the two layers are arranged parallel to one another at such a distance that there is a capillary-active gap between the two layers.

So-called carrier-bound tests are often used for the qualitative or quantitative analytical determination of components of body fluids, in particular of blood. In these the reagents are embedded in corresponding layers of a solid carrier which is contacted with the sample. If a target analyte is present, the reaction of the liquid sample and reagents leads to a detectable signal, in particular a colour change which can be evaluated visually or with the aid of an instrument, usually by reflection photometry.

Test elements or test carriers are often in the form of test strips which are essentially composed of an elongate support layer made of plastic material and detection layers which are applied thereto as test fields. However, test carriers are also known which are in the shape of small quadratic or rectangular plates.

Test elements for clinical diagnostics that are evaluated visually or by reflection photometry are frequently constructed, like electrochemical sensors and biosensors, such that the sample application zone and the detection zone are arranged one above the other in a vertical axis. This mode of construction is problematic. When the test strip loaded with sample has to be inserted into an instrument, for example a reflection photometer, for measurement, potentially infectious sample material can come into contact with parts of the instrument and may contaminate them. Furthermore volumetric dosing can only be achieved with difficulty especially in cases in which the test strips are used by untrained persons for example in the self-control of blood sugar by diabetics.

Test elements have recently become available which provide a capillary channel or gap which solves at least some of the described problems.

EP-A-0 287 883 describes a test element which utilizes a capillary interspace between the detection layer and an inert carrier for volumetric dosing. The test element is dipped into the sample to be examined to fill the capillary space requiring large sample volumes which is why this type of volumetric dosing is primarily suitable for the examination of sample material that is present in excess such as urine. There is no spatial separation between the site of sample application and the site of detection.

EP-B-0 034 049 concerns a test element in which the sample is applied to a central sample application site for example an opening in a cover and is transported by capillary force to several detection zones which are spatially separated from the sample application site. The central position of the sample application site in a test element according to EP-B-0 034 049 does not solve the problem of instrument hygiene as described above.

In the described capillary gap test elements, the capillary gap is in each case formed by continuous one-part layers. It would be desirable that at least one layer would be composed of several adjacent parts made of different materials especially in cases where the capillary transport is over not inconsiderable distances such as more than 10 mm, especially to deal with the problem of instrument hygiene. The different materials could then be used for zones with different tasks such as for transport zones, reservoir zones and/or reaction zones. The use of different materials would then enable a specific optimization of the material properties with regard to their desired purpose. However, this poses the problem that even very slight changes in the dimensions of the gap or channel responsible for the capillary effect lead to an abrupt termination of the capillarity. Increases in the cross-section in a micrometer range are adequate for this. Maintenance of capillary continuity at the junction of different zones is a problem which to the knowledge of the applicant has up to now not been satisfactorily solved.

The object of the present invention was therefore to eliminate the disadvantages of the prior art.

This is achieved by the subject matter of the invention as characterized in the patent claims.

The invention concerns a device for the capillary transport of a liquid between two opposite essentially planar layers, in which the layers are arranged at a distance parallel to one another so that there is a capillary-active gap between the two layers, which is characterized in that at least one of the two layers contains at least two discrete adjacent parts and that the capillary-active transport of the liquid is possible beyond the common boundary of the parts that lie in one layer. The opposite planar layers are preferably provided with hydrophilic properties.

In this connection hydrophilic surfaces are water-attracting surfaces. Aqueous samples, also including blood, spread well on such surfaces. Such surfaces are characterized among others in that a water drop placed on it forms an acute rim angle or contact angle at the interface. In contrast an obtuse rim angle is formed at the interface between a water drop and surface on hydrophobic i.e. water repellent surfaces.

The rim angle which is a result of the surface tensions of the test liquid and of the surface to be examined is a measure of the hydrophilicity of a surface. Water for example has a surface tension of 72 mN/m. If the value of the surface tension of the observed surface is much below this value i.e. more than 20 mN/m below this value, then the wetting is poor and the resulting rim angle is obtuse. Such a surface is referred to as hydrophobic. If the surface tension approximates the value which is found for water then the wetting is good and the rim angle is acute. If, in contrast, the surface tension is the same as or higher than that of the value found for water, then the drop runs and there is a total spreading of the liquid. It is then no longer possible to measure a rim angle. Surfaces which form an acute rim angle with water drops or on which a total spreading of a water drop is observed are referred to as hydrophilic.

The ability of a capillary to aspirate a liquid depends on the wettability of the channel surface with the liquid. This means for aqueous samples that a capillary should be manufactured from a material whose surface tension almost reaches 72 mN/m or exceeds this value.

Sufficiently hydrophilic materials for the construction of a capillary which rapidly aspirates aqueous samples are for example glass, metal or ceramics. However, these materials are unsuitable for use in test carriers since they have some severe disadvantages such as risk of breaking in the case of glass or ceramics or change in the surface properties with time in the case of numerous metals. Therefore plastic foils or moulded parts are usually used to manufacture test elements. As a rule the plastics used hardly exceed a surface tension of 45 mN/m. Even with the, in a relative sense, most hydrophilic plastics such as polymethylmethacrylate (PMMA) or polyamide (PA) it is only possible—if at all—to construct slowly sucking capillaries. Capillaries made of hydrophobic plastics such as for example polystyrene (PS), polypropylene (PP) or polyethylene (PE) essentially do not suck aqueous samples. Consequently it is necessary to endow the plastics used as a construction material for test elements with capillary active channels with hydrophilic properties i.e. to hydrophilize them.

In a preferred embodiment of the analytical test element according to the invention at least one, but preferably two and especially preferably two opposite surfaces which form the inner surface of the channel capable of capillary liquid transport are hydrophilized. If more than one surface is hydrophilized then the surfaces can either be made hydrophilic using the same or different methods. Hydrophilization is particularly necessary when the materials that form the capillary active channel, in particular the carrier, are themselves hydrophobic or only very slightly hydrophilic because they are for example composed of nonpolar plastics. Nonpolar plastics such as for example polystyrene (PS), polyethylene (PE), polyethylene terephthalate (PET) or polyvinyl chloride (PVC) are advantageous as carrier materials because they do not absorb the liquids to be examined and thus the sample volume can be effectively utilized by the detection layer. The hydrophilization of the surface of the capillary channel enables a polar, preferably aqueous, sample liquid to readily enter the capillary channel and be rapidly transported there to the detection element or to the site of the detection element where the detection takes place.

Ideally the hydrophilizaton of the surface of the capillary channel is achieved by using a hydrophilic material in its manufacture which, however, cannot itself absorb the sample liquid or only to a negligible extent. In cases where this is not possible a hydrophobic or only very slightly hydrophilic surface can be hydrophilized by suitable coating with a stable hydrophilic layer that is inert towards the sample material for example by covalently binding photoreactive hydrophilic polymers onto a plastic surface by applying layers containing wetting agents or by coating surfaces with nanocomposites by means of sol-gel technology. Furthermore it is also possible to achieve an increased hydrophilicity by thermal, physical or chemical treatment of the surface.

The hydrophilization is quite especially preferably achieved by using thin layers of oxidized aluminium. These layers are either applied directly to the desired components of the test element for example by vacuum coating the work pieces with metallic aluminium and subsequently oxidizing the metal, or by using metal foils or metal-coated plastics for the construction of the test carriers which also have to be oxidized to achieve the desired hydrophilicity. In this case metal layer thicknesses of 1 to 500 nm are adequate. The metal layer is subsequently oxidized to form the oxidized form in which case above all oxidation in the presence of water vapour or by boiling in water have proven to be especially suitable methods in addition to electrochemical, anodic oxidation. The oxide layers formed in this manner are between 0.1 and 500 nm, preferably between 10 and 100 nm thick depending on the method. Larger layer thicknesses of the metal layer as well as of the oxide layer can in principle be realised in practice but do not exhibit any additional advantageous effects.

The adjacent parts of the device according to the invention which together form a layer, are preferably manufactured from different materials and additionally serve different purposes. For example one part can be manufactured from a plastic foil that is inert towards liquid, whereas the second and optionally further parts are manufactured from materials which can interact with the sample liquid in a characteristic manner. If for example the device according to the invention is to be used for the visual or photometric determination of an analyte in a liquid sample, one part of the said layer can be designed as a detection element which can contain all reagents and auxiliary substances required for a specific detection reaction. Such detection elements are known to a person skilled in the art and do not need to be elucidated here in more detail. The detection element is preferably composed of a foil whose side facing the channel is coated with the required reagents and auxiliary agents.

The two adjacent components of the layer must be assembled such that both abut each other in the final device so that liquid transport in the capillary is not interrupted at the junction between the parts by for example an unfavourable change of the capillary cross-section which is also understood to include an interruption of a continuous boundary surface of the capillary. The dimensions of the said components must be mutually matched for this purpose.

In order to avoid interruption of the capillary liquid transport in the capillary channel it has proven to be preferable to attach a thin flexible inert foil to the side facing the channel capable of capillary liquid transport of one part of the layer, which is composed of at least two parts, and the foil extends over the entire length of the said part, covers the capillary channel over its entire width and partially covers the neighbouring part of the layer on the side facing the channel capable of capillary liquid transport. Thus the foil layer covers the zone connecting the two parts and hence enables maintenance of the capillary continuity at this sensitive site. The material and optionally the hydrophilizing coating of the foil which is referred to as gap cover foil in the following can essentially correspond to that already described above for other components of the device according to the invention. Since the foil only covers a part of the layer, a change in the capillary cross-section occurs at the site where the foil ends due to the thickness of the foil. The foil must not exceed a certain thickness to ensure this change in cross-section does not lead to a break-down of capillary flow. A foil thickness of less than 5 $\mu$m has turned out to be the maximum permissible thickness. A thickness of less than 1 $\mu$m is particularly preferred.

Such thin foils are difficult to handle for example because they tear easily, are difficult to coat, and crease and therefore cause manufacturing problems which lead to higher production costs. For this reason it is preferable to use thicker foils with foil thicknesses between 5 and 20 $\mu$m. It was surprisingly found that for an especially preferred embodiment of the device according to the invention a flexible inert foil can be attached to the side of a part of the multipart layer facing the channel capable of capillary liquid transport which extends over the entire length of the said part, covers the capillary channel over the entire width and which is at least partially enclosed between the opposite surfaces of the adjacent parts so that the capillary liquid transport does not break down at the common junction between the parts. The material and optionally the hydrophilizing coating of the foil can essentially correspond to that which was already described above for the other components of the device according to the invention. Since in this particularly preferred variant of the subject matter of the invention the foil does not overlap the part of the layer which adjoins the foil coated part, the use of the gap cover foil does not necessarily lead to a change in the cross-section of the capillary channel. Therefore in this case foils with larger thicknesses can be used. Thicknesses of 5 to 20 $\mu$m have proven to be preferable and in particular of 5 to 15 $\mu$m.

The invention is elucidated in more detail by FIGS. 1 to 3 and by the following examples.

Figure 1:
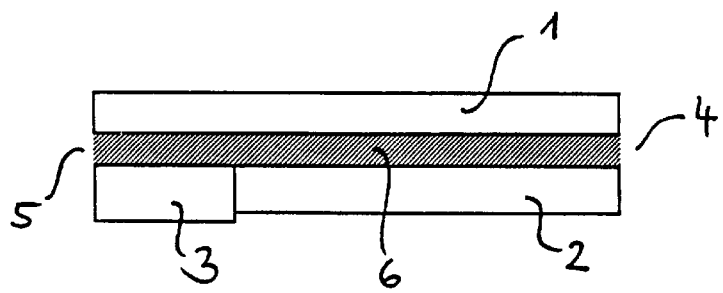
FIG. 1 shows a schematic cross-section of a particularly preferred embodiment of the device according to the invention.

The numbers in the Figures denote:
1 carrier layer
2 cover layer 1
3 cover layer 2
4 sample application opening
5 vent opening
6 capillary channel
7 gap cover foil A cross-sectional view of a particularly preferred embodiment of the device according to the invention is shown schematically in FIG. 1. The device is composed of a carrier layer (1) which is shaped such that where it is covered with the cover layers 1 (2) and 2 (3) it forms a capillary channel (6) with these. For example a recess can be stamped or milled into the carrier layer (1) or into the two cover layers 1 (2) and 2 (3) to form the capillary channel (6). If planar layers (1,2,3) are used, the capillary channel (6) can also be formed by an intermediate layer (not shown).

The intermediate layer can be manufactured from a double-sided adhesive tape which, in addition to determining the geometry of the capillary channel, also has the purpose of joining the other components i.e. carrier layer (1), cover layer 1(2) and 2(3) that are involved in forming the capillary-active zone (6). In the region of the capillary channel (6) the intermediate layer has a recess which determines the length and width of the channel (6). Its height is determined by the thickness of the intermediate layer.

In the embodiment shown a sample application opening (4) is provided on one side of the capillary channel (6). On the side of the capillary channel (6) that is opposite to the sample application opening (4) there is a vent opening (5) which allows air to escape when the capillary channel (6) is filled with sample liquid.

The capillary zone (6) extends from the sample application opening (4) to the opposite end of the second cover layer (3). The sample application opening (4) and vent opening (5) limit the capillary-active region (6) in the direction of capillary transport.

Cover layers 1(2) and 2(3) are mounted next to one another end to end such that the capillary channel (6) extends continuously from the sample application opening (4) to the vent opening (5).

Figure 2:
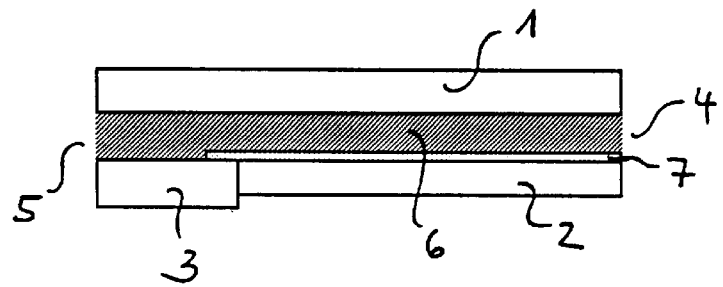
FIG. 2 shows a schematic cross-section through a further particularly preferred embodiment of the device according to the invention.
Figure 3:
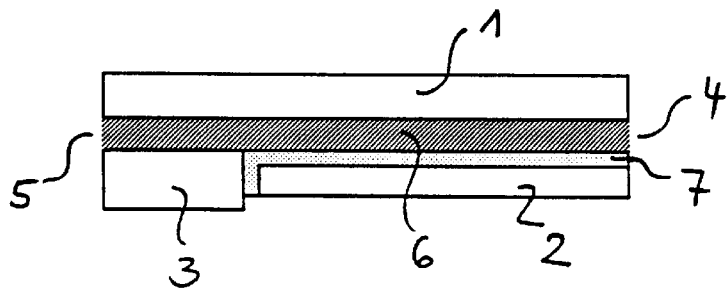
FIG. 3 shows a schematic cross-section through a particularly preferred embodiment of the device according to the invention.

In FIGS. 2 and 3 cross-sectional views show schematically how a break down of the capillary-active region (6) can be reliably avoided at the contact site between the cover layers 1(2) and 2(3) by using a cover gap foil (7). Furthermore the cover gap foil (7) can be provided with a hydrophilic surface on the side facing the capillary channel (6) which facilitates capillary transport of a sample liquid drop from the sample application opening (4) to the vent opening (5).

In FIG. 2 the cover gap foil (7) covers the cover layer 1(2) over its entire length and also partially overlaps the cover layer 2(3) which leads there to a change in the cross-section of the capillary-active zone (6).

As an alternative to the embodiment shown schematically in FIG. 2, FIG. 3 shows how the cover gap foil (7) can ensure a capillary continuity between the cover layer 1(2) and 2(3). In the quite especially preferred embodiment shown the cover gap foil (7) is enclosed between the cover layers 1(2) and 2(3) and thus does not overlap the cover layer 2(3).

EXAMPLE 1

Manufacture of the Device According to the Invention

A double-sided adhesive tape with a thickness of 100 μm is glued onto a 350 μm thick foil of polyethylene terephthalate (Melinex®, ICI, Frankfurt am Main, Germany) coated with a 30 nm thick layer of aluminium which was completely oxidized with water vapour. The foil has a length of 25 mm and is 5 mm wide. A central notch-shaped recess of 1 mm width and 2 mm length is located on one of the short sides. The adhesive tape has a punched hole of 2 mm width and more than 15 mm length which defines the dimensions of the capillary channel. The length of the punched hole is selected to be slightly larger than the desired length of the capillary-active channel which is determined by its cover in order to ensure venting of the channel during filling with sample liquid. A 3 mm long and 5 mm wide detection film is glued onto the side of the adhesive tape which provides the venting at a distance of 1 mm from the end of the punched hole. A film is used as the detection film as is known from the German Patent Application No. P 196 29 656.0. The detection film is specific for the detection of glucose. A 12 mm long and 5 mm wide cover layer is glued onto the region of the adhesive tape that is still open between the notch-shaped recess and detection film so that the cover layer and detection film abut one another. The cover layer is composed of a 150 μm thick polyethylene terephthalate foil provided on one side with adhesive onto which a 6 μm thick polyethylene terephthalate foil (both: Hostaphan®, Hoechst, Frankfurt am Main, Germany) coated with a 30 nm thick oxidized aluminium layer on the side facing the capillary channel is glued. In this case the thinner foil extends ca. 500 μm beyond the thicker foil on the side facing the detection film. When the cover layer is mounted on the adhesive tape care must be taken that the protruding end of the thinner foil comes to lie between the detection element and the thicker foil of the cover layer. In order to cover areas of the adhesive foil that are still exposed, these are covered with a 175 μm thick Melinex® foil without, however, covering functional areas.

The test element obtained in this manner has a capillary channel of 15 mm length, 2 mm width and 0.1 mm height. The channel can take up 3 μl sample liquid. An area of 3 mm×2 mm of the detection film is wetted by the sample.

EXAMPLE 2

Measurement of the blood glucose concentration with the aid of the test element from example 1

The sample application side of the test element from example 1 is placed on a drop of sample liquid. The capillary of the test element automatically fills with sample within 2 s. If glucose is present in the sample a colour development is visible in the detection film after a few seconds. The end point of the reaction is reached after ca. 30 to 35 s. The colour obtained can be correlated with the glucose concentration of the sample and either evaluated visually or by reflection photometry.

What is claimed is:

1. Device for the capillary transport of a liquid between two opposite, essentially planar layers, in which the two layers are arranged parallel to one another at such a distance that there is a capillary-active gap forming a capillary channel between the two layers, wherein at least one of the two layers contains at least two discrete adjacent cover layers each having an end and being positioned next to one another end to end and a flexible inert foil of less than 5 µm thick is attached to a side facing the channel capable of capillary liquid transport, which is composed of the at least two cover layers, and which extends over an entire length of one of the said cover layers, covers the capillary channel over its entire width and partially covers the adjacent cover layer on the side facing the channel capable of capillary liquid transport, wherein the flexible, inert foil is hydrophilized on a surface facing the capillary gap and a layer of oxidized aluminium is used for the hydrophilization.

2. Device for the capillary transport of a liquid between two opposite, essentially planar layers, in which the two layers are arranged parallel to one another at such a distance that there is a capillary-active gap forming a capillary channel between the two layers, wherein at least one of the two layers contains at least two discrete adjacent cover layers each having an end and being positioned next to one another end to end and a flexible inert foil of less than 5 µm thick is attached to a side facing the channel capable of capillary liquid transport, which is composed of the at least two cover layers, and which extends over the entire length of one of the said cover layers, covers the capillary channel over its entire width and partially covers the adjacent cover layer on a side facing the channel capable of capillary liquid transport.

3. Device as claimed in claim 2, wherein the flexible, inert foil is hydrophilized on the surface facing the capillary gap.

4. Device as claimed in claim 2, wherein the flexible inert foil is at least partially enclosed between the two opposite surfaces of the two cover layers of the said layer.

5. Device as claimed in claim 2, wherein the two adjacent cover layers are composed of different materials.

6. Device as claimed in claim 5, wherein the flexible inert foil is at least partially enclosed between the two opposite surfaces of the two cover layers.

7. Device for the capillary transport of a liquid between two opposite, essentially planar layers, in which the two layers are arranged parallel to one another at such a distance that there is a capillary-active gap forming a capillary channel between the two layers, wherein at least one of the two layers contains at least two discrete adjacent cover layers each having an end and being positioned next to one another end to end and a flexible inert foil of less than 5 µm thick is attached to a side facing the channel capable of capillary liquid transport, which is composed of the at least two cover layers, and which extends over the entire length of one of the said cover layers, covers the capillary channel over its entire width and partially covers the adjacent cover layer on the side facing the channel capable of capillary liquid transport, wherein the flexible, inert foil is hydrophilized on a surface facing the capillary gap and a layer of oxidized aluminium is use for the hydrophilization.

8. Device as claimed in claim 7, wherein the foil has a thickness of 5 to 20 µm inclusive.

9. Device as claimed in claim 8, wherein the flexible, inert foil is hydrophilized on the surface facing the capillary gap.

10. Device for the capillary transport of a liquid between two opposite, essentially planar layers, in which the two layers are arranged parallel to one another at such a distance that there is a capillary-active gap between the two layers, wherein at least one of the two layers contains at least two discrete adjacent cover layers each having an end and being positioned next to one another end to end and a flexible inert foil is attached to a side facing the gap capable of capillary liquid transport of one part of the layer, which is composed of at least two cover layers, and which extends over the entire length of one of the said cover layers, covers the capillary gap over its entire width and is at least partially enclosed between the two opposite ends of the two cover layers of the said layer.

11. Device as claimed in claim 10, wherein the two adjacent cover layers of a layer are composed of different materials.

12. Device as claimed in claim 11, wherein the foil has a thickness of 5 to 20 µm inclusive.

13. Device as claimed in claim 11, wherein the flexible, inert foil is hydrophilized on the surface facing the capillary gap.

14. Device for the capillary transport of a liquid between two opposite, essentially planar layers, in which the two layers are arranged parallel to one another at such a distance that there is a capillary-active gap between the two layers, wherein at least one of the two layers contains at least two discrete adjacent cover layers each having an end and being positioned next to one another end to end and a flexible inert foil is attached to a side facing the gap capable of capillary liquid transport of one part of the layer, which is composed of at least two cover layers, and which extends over the entire length of one of the said cover layers, covers the capillary gap over its entire width and is at least partially enclosed between the ends of the two cover layers of the said layer, wherein the two adjacent cover layers of a layer are composed of different materials, the flexible, inert foil is hydrophilized on the surface facing the capillary gap, and a layer of oxidized aluminum is used for the hydrophilization.

15. A device for the capillary transport of a liquid, the device comprising:
   a first layer,
   a second layer spaced-apart from the first layer a distance sufficient to form a capillary channel having a predetermined width, wherein the second layer includes a first cover layer and a second discrete cover layer, the first and second cover layers each having an end and being positioned adjacent to one another in an end to end relationship, and
   a foil positioned in the capillary channel, the foil extending over the entire width of the capillary channel, being attached to and extending over the entire length of the first cover layer, and extending over a portion of the second cover layer.

16. Device as claimed in claim 15, wherein the two cover layers are composed of different materials.

17. Device as claimed in claim 15, wherein the foil has a thickness of 5 to 20 µm.

18. Device as claimed in claim 15, wherein the foil is hydrophilized on the surface facing the capillary channel.

19. A device for the capillary transport of a liquid, the device comprising:
   a first layer,
   a second layer spaced-apart from the first layer a distance sufficient to form a capillary channel having a predetermined width, wherein the second layer includes a first cover layer and a second discrete cover layer, the first and second cover layers being positioned adjacent to one another in an end to end relationship, and
   a foil positioned in the capillary channel, the foil extending over the entire width of the capillary channel, extending over the entire length of the first cover layer, and extending over a portion of the second cover layer, wherein the foil is hydrophilized on the surface facing the capillary channel and a layer of oxidized aluminum is used for the hydrophilization.

20. Device for the capillary transport of a liquid, the device comprising:

a first layer, a second layer spaced-apart from the first layer a distance sufficient to form a capillary channel having a predetermined width, wherein the second layer includes a first cover layer and a second discrete cover layer, the first and second cover layers being positioned adjacent to one another in an end to end relationship, and a foil positioned in the capillary channel, the foil extending over the entire width of the capillary channel, extending over the entire length of the first cover layer, and is at least partially enclosed between the first and second cover layers.

21. Device as claimed in claim 20, wherein the cover layers are composed of different materials.

22. Device as claimed in claim 20, wherein the foil has a thickness of 5 to 20 $\mu$m.

23. Device as claimed in claim 20, wherein the foil is hydrophilized on the surface facing the capillary channel.

24. Device for the capillary transport of a liquid, the device comprising:

a first layer, a second layer spaced-apart from the first layer a distance sufficient to form a capillary channel having a predetermined width, wherein the second layer includes a first cover layer and a second discrete cover layer, the first and second cover layers being positioned adjacent to one another in an end to end relationship, and a foil positioned in the capillary channel, the foil extending over the entire width of the capillary channel, extending over the entire length of the first cover layer, and is at least partially enclosed between the first and second cover layers, wherein the foil is hydrophilized on the surface facing the capillary channel and a layer of oxidized aluminum is used for the hydrophilization.

* * * * *